United States Patent
Landuyt

[19]
[11] Patent Number: 6,149,632
[45] Date of Patent: Nov. 21, 2000

[54] SELF-SEALING SEPTA

[75] Inventor: Christophe Van Landuyt, London, United Kingdom

[73] Assignee: Smiths Industries Public Limited Company, London, United Kingdom

[21] Appl. No.: 09/280,071

[22] Filed: Mar. 29, 1999

[30] Foreign Application Priority Data

Apr. 17, 1998 [GB] United Kingdom .................... 9808140

[51] Int. Cl.$^7$ ...................................... A61M 5/00
[52] U.S. Cl. ........................................... 604/256; 604/201
[58] Field of Search ..................... 604/256, 167, 604/169, 247, 201, 244; 137/849, 843

[56] References Cited

U.S. PATENT DOCUMENTS

| | | |
|---|---|---|
| 4,436,519 | 3/1984 | O'Neill . |
| 4,895,565 | 1/1990 | Hillstead ................. 604/167 |
| 4,929,235 | 5/1990 | Merry et al. . |
| 5,000,745 | 3/1991 | Guest et al. .............. 604/256 |
| 5,154,701 | 10/1992 | Cheer et al. ............. 604/167 |
| 5,643,227 | 7/1997 | Stevens ................... 604/264 |
| 5,738,334 | 4/1998 | Proni ....................... 251/149.1 |
| 5,779,697 | 7/1998 | Glowa et al. ............ 606/185 |
| 5,843,046 | 12/1998 | Motisi et al. ............ 604/256 |

FOREIGN PATENT DOCUMENTS

| | | |
|---|---|---|
| 0 230 751 | 8/1987 | European Pat. Off. . |
| 0 370 720 | 5/1990 | European Pat. Off. . |
| WO 94/01149 | 1/1994 | WIPO . |

*Primary Examiner*—Sharon Kennedy
*Assistant Examiner*—Kevin C. Sirmons
*Attorney, Agent, or Firm*—Pollock, Vande Sande & Amernick, R.L.L.P

[57] ABSTRACT

A self-sealing needle injection hub has two resilient, elastomeric sealing members mounted adjacent one another in a housing, both having pierced passages through which a needle can be inserted. The outer member is thick and relatively rigid; the inner member is thinner and flexible. Both members are radially compressed by the housing, the inner member bowing away from the outer member at its center. The action of withdrawing a needle from the hub, combined with the pressure of blood on the inner member, maintains the inner member flat against the outer member, thereby further compressing the passage through the inner member.

9 Claims, 1 Drawing Sheet

SELF-SEALING SEPTA

BACKGROUND OF THE INVENTION

This invention relates to self-sealing septa.

Self-sealing septa are used in medico-surgical and other apparatus to form a seal with the outside of a needle or similar device inserted in the septa, which closes when the needle is withdrawn. For example, a septum in the hub of a catheter might seal with a needle used to introduce the catheter into the body of the patient. When the needle is withdrawn from the catheter, the septum closes to prevent escape of blood through the catheter hub.

One problem with self-sealing septa is that the rubber-like material of the septum changes characteristics as it ages and may make a less effective seal. This is especially the case where the septum is stored for prolonged periods with a needle, or the like, inserted in the septum. In such circumstances, the material of the septum tends to set into its deformed state and produces a lower sealing force when the needle is withdrawn. Attempts have been made to overcome this problem, such as described in, for example, EP 415653. Although this arrangement can help alleviate the problem, it is not universally satisfactory.

SUMMARY OF THE INVENTION

It is an object of the present invention to provide improved self-sealing septa.

According to the present invention there is provided a self-sealing septum arranged to receive an elongate member extending axially therein and to seal closed when the elongate member is withdrawn, the septum including a housing containing a first member extending transversely across the housing and a second flexible member adjacent the first member. The second member having a passage therethrough within which the elongate member is received, and the second member is displaceable from a domed shape where the center of the second member is spaced away from the first member, to a flat shape where the second member lies flat against the first member thereby causing a radial pressure to be exerted about the passage through the second member tending to close the passage.

Preferably, the first and second members are of a resilient elastomeric material. The first member is preferably thicker than the second member. The passage through the second member may be formed by piercing without removal of material. The first member may have a passage therethrough, which is preferably formed by piercing without removal of material. The natural diameter of the first member and of the second member are preferably larger than the internal diameter of the housing. The housing may be attached with a catheter.

An injection hub according to the present invention, will now be described, by way of example, with reference to the accompanying drawing.

DETAILED DESCRIPTION OF THE PREFERRED EMBODIMENT

Figure 1:
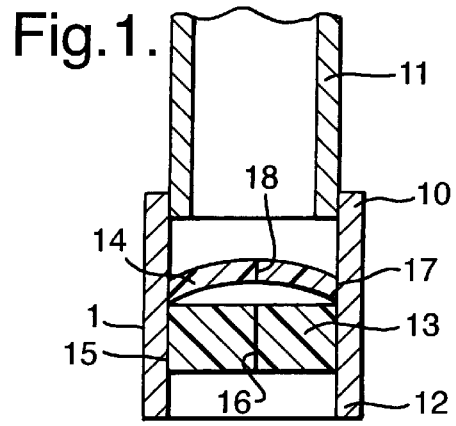
FIG. 1 is a cross-sectional side elevation view of the hub before use.

The hub or self-sealing septum comprises an outer cylindrical housing 1 of a rigid plastics material. The upper end 10 of the housing is attached to a dialysis catheter 11, or to some other tubing or the like; the lower end 12 of the housing is open. The housing 1 contains two sealing members 13 and 14.

The lower, or outer, sealing member 13 extends transversely across the housing 1 and is of a rubber or a similar resilient, elastomeric material. The lower sealing member 13 is relatively thick so that it is relatively rigid against axial force exerted at its center. The sealing member 13 is fixed around its outer edge 15 with the housing 1 by any conventional means, such as an adhesive or by locating within a recess, or by some other mechanical means. The sealing member 13 has a central passage 16 therethrough formed by piercing the member without removing any material, so that the passage is normally closed by the resilience of the material. The natural diameter of the lower sealing member 13 is slightly larger than the internal diameter of the housing 1 so that the sealing member is compressed radially by the housing 1, which helps close the passage 16 when there is no needle present.

The upper, or inner, sealing member 14 may be of the same material as the lower member 13 but is thinner, being about half its thickness or less, so that the upper member is flexible axially at its center. The outer edge 17 of the upper sealing member 14 is attached to the inside of the housing 1 directly adjacent the upper surface of the lower sealing member 13. The natural diameter of the upper sealing member 14 is slightly larger than the internal diameter of the housing 1. The upper sealing member 14 also has a central passage 18 extending through it, the passage being formed without removal of material so that it is normally closed by the resilience of the material of the member. The central part of the upper sealing member 14 is unattached to the lower sealing member 13.

Prior to use, and where no pressure is applied within the catheter 11, the upper sealing member 14 has a domed shape, as shown in FIG. 1, forming a convex upper or inner surface, with its center being spaced from the center of the lower sealing member 13.

Figure 2:
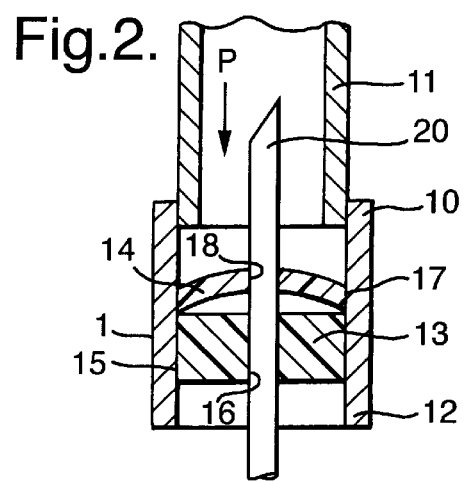
FIG. 2 is a cross-sectional side elevation view of the hub with a needle inserted.

When a needle 20 is inserted in the hub, as shown in FIG. 2, it extends through the passages 16 and 18 through the two sealing members 13 and 14. The needle 20 has a sharply pointed bevelled tip 21, which is located above the two sealing members 13 and 14, so that the tip of the needle opens into the catheter 11. The diameter of the needle 20 expands the passages 16 and 18 through the two sealing members 13 and 14 and this causes a radial, inwards pressure to be exerted on the outside of the needle by the material of the sealing members. Because the diameter of the flexible sealing member 14 is larger than the internal diameter of the housing 1, once displaced slightly from a flat state, there is a tendency for it to adopt the domed shape where there is a lower radial compressive force. The lower sealing member 13 prevents downwards displacement of the center of the upper sealing member 14. With the needle 20 inserted, there is additional radial compressive force within the upper sealing member 14, ensuring that it maintains the domed shape; friction with the outside of the needle also helps maintain the domed shape against blood pressure P within the catheter 11. When pressure P is exerted by blood within the catheter 11, it bears on the upper surface of the upper sealing member 14 ensuring that there is an effective sealing force exerted at the passage 18 with the outside of the needle 20.

Figure 3:
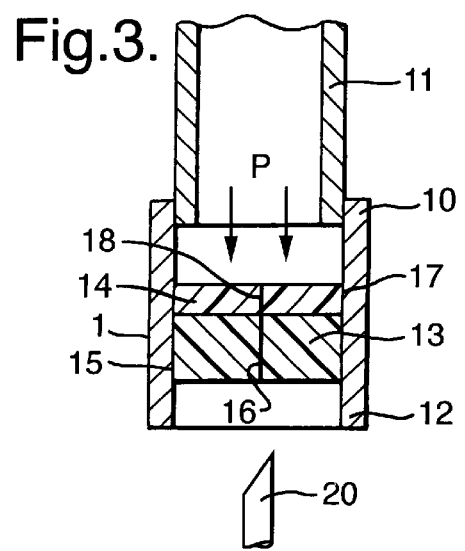
FIG. 3 is a cross-sectional side elevation view of the hub with the needle removed.

When the needle 20 is pulled out of the septum, as shown in FIG. 3, that is, in a downward direction, the absence of the needle means that there is less force maintaining the flexible sealing member 14 in its domed state. Because of this, the pressure of blood P in the catheter 11 exerted on the upper surface of the flexible sealing member 14 is sufficient to flatten the sealing member against the upper surface of the lower sealing member 13. The action of pulling out the needle 20 may also have the effect of applying a frictional force to the passage 18 through the upper sealing member 14, which helps pull it down in the center. In this flat state, the radial forces within the upper member 14 are relatively high, causing a high closing force about the passage 18 through the member, which increases the sealing of this passage. The upper sealing member 14 maintains this flat state until the needle 20 is reinserted in the septum. The thickness of the lower sealing member 13 is sufficient so that its center is not deflected significantly during insertion or withdrawal of the needle 20.

With the needle 20 withdrawn, therefore, the passage 16 through the lower sealing member 13 is also closed. The closure of the passage 16 through the lower sealing member 13 may not, however, be complete and entirely effective if, for example, the septum has been stored with the needle 20 inserted for a prolonged period. However, the additional sealing force exerted on the upper sealing member 14 caused by its displacement from a domed to a flat state, is sufficient to ensure an effective seal.

It will be appreciated that the septum may be used to form a seal with elongate members other than needles.

What is claimed is:

1. A self-sealing septum comprising: a housing; a first member located within said housing and extending transversely across said housing; and a second flexible member located within said housing adjacent said first member, said second member having a central passage therethrough, formed by piercing without removal of material, for receiving an elongate member inserted in said septum, wherein said second member is displaceable from a domed shape where the center of said second member is spaced away from said first member, to a flat shape where said second member lies flat against said first member thereby causing a radial pressure to be exerted about the passage through said second member tending to close said passage, and wherein said first member is thicker than said second member.

2. A septum according to claim 1, wherein said first member is of a resilient elastomeric material.

3. A septum according to claim 1, wherein said second member is of a resilient elastomeric material.

4. A septum according to claim 1, wherein said first member has a passage therethrough.

5. A septum according to claim 1, wherein the natural diameter of said first member is larger than the internal diameter of said housing.

6. A septum according to claim 1, wherein the natural diameter of said second member is larger than the internal diameter of said housing.

7. A septum according to claim 1, wherein said housing is attached with a catheter.

8. A self-sealing septum comprising: a housing; a first resilient elastomeric member within said housing and extending transversely across said housing; and a second flexible member within said housing adjacent said first member, wherein said second member is thinner than said first member, wherein said second member has a natural diameter larger than the internal diameter of the housing, wherein said second member has a passage therethrough for receiving a needle inserted in said septum through said first member, and wherein said second member is displaceable from a domed shape where the center of said second member is spaced away from said first member, to a flat shape when said needle is withdrawn from said septum, so that said second member lies flat against said first member thereby causing a radial pressure to be exerted about said passage through said second member tending to close said passage.

9. A self-sealing septum comprising: a housing; a first member located within said housing and extending transversely across said housing; and a second flexible member located within said housing adjacent said first member, said second member having a central passage therethrough, formed by piercing without removal of material, for receiving an elongate member inserted in said septum, wherein said second member is displaceable from a domed shape where the center of said second member is spaced away from said first member, to a flat shape where said second member lies flat against said first member thereby causing a radial pressure to be exerted about the passage through said second member tending to close said passage, wherein said first member has a passage therethrough and wherein said passage through said first member is formed by piercing without removal of material.

* * * * *